United States Patent [19]

Kihn

[11] 4,315,510

[45] Feb. 16, 1982

[54] METHOD OF PERFORMING MALE STERILIZATION

[75] Inventor: Harry Kihn, Lawrenceville, N.J.

[73] Assignee: Cooper Medical Devices Corporation, Newtown, Pa.

[21] Appl. No.: 39,652

[22] Filed: May 16, 1979

[51] Int. Cl.³ .............................................. A61B 17/36
[52] U.S. Cl. .................................. 128/303.1; 128/402
[58] Field of Search ........... 128/303.1, 303.17, 303.13, 128/804, 306, 1.3, 24.1, 402, 400, 399

[56] References Cited

U.S. PATENT DOCUMENTS

| 3,095,880 | 7/1963 | Haagensen | 128/804 |
| 3,831,607 | 8/1974 | Lindemann | 128/804 X |
| 4,103,688 | 8/1978 | Edwards | 128/303.17 |

FOREIGN PATENT DOCUMENTS 2821264 11/1978 Fed. Rep. of Germany ... 128/303.1

OTHER PUBLICATIONS

Gunn et al. "Effect of Microwave Radiation on the Male endocrine System".
De Lateur et al. "Muscle Heating in Human Subjects with 915 MHz Microwave Contact Applicator".
T. S. Ely et al. "Heating Charac. of Lab. Animals Exposed to Ten CM. Microwaves" IEEE Trans on BME pp. 123-136 (10-1964).
M. S. Fahim et al. "Heat in Male Contraception" *Contraception* May 1975 vol. 11 No. 5 pp. 549-562.

*Primary Examiner*—Michael H. Thaler
*Attorney, Agent, or Firm*—Austin R. Miller

[57] ABSTRACT

A method for sterilizing a male by coagulating an anatomical element using an instrument having a body with two members adapted for closing towards each other and holding therebetween an anatomical element, and a waveguide constructed to emit electromagentic radiation at a predetermined microwave frequency suitable for coagulation of an anatomical element, the waveguide disposed on at least one of the body members, comprising the steps of holding an anatomical element between the body members closed towards each other at a predetermined pressure causing emission of electromagnetic radiation from the waveguide in one of the body members towards the remaining body member, the radiation being emitted at a frequency to selectively permanently cauterize only muscle tissue portions of the anatomical element held between the body members without significant damage to fatty tissue portions of the anatomical element held between the body members; and subjecting the held anatomical element to the emitted waveguide radiation for only a period of time sufficient to coagulate the muscle tissue portions of the anatomical element.

13 Claims, 10 Drawing Figures

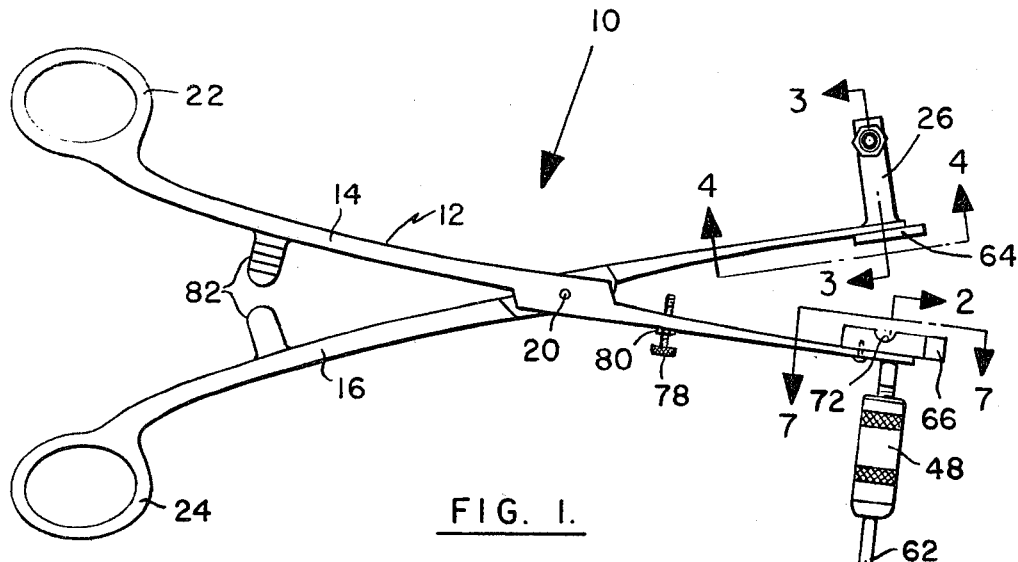
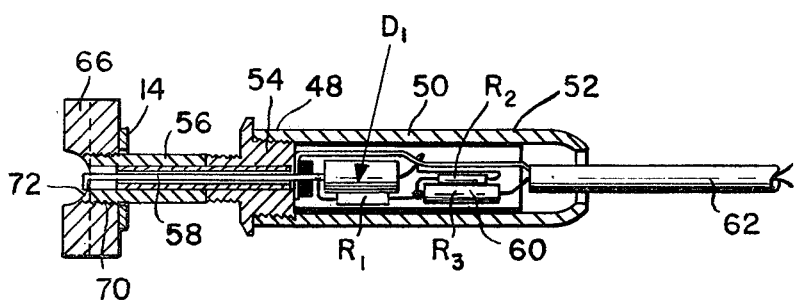
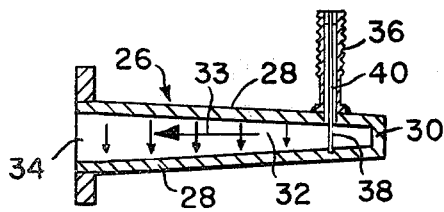
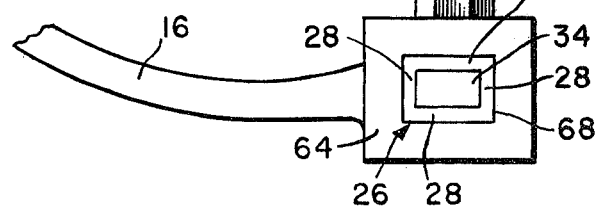
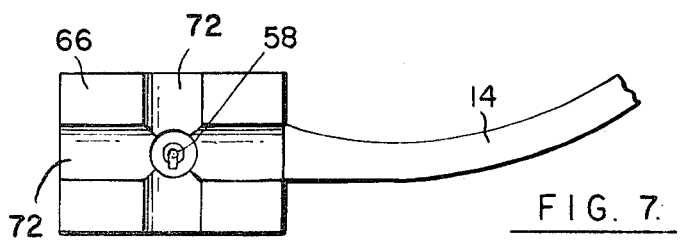

METHOD OF PERFORMING MALE STERILIZATION

BACKGROUND OF THE INVENTION

The present invention relates to a method for human sterilization, and more particularly to a method for sterilization of the male by coagulation of the vas.

Tubal ligation instruments have found worldwide acceptance for a variety of purposes but in particular have been used for sterilization of the male. In many areas of the world the question of population control has become an essential issue, and such instruments have found wide utilization.

In the U.S. Pat. No. 3,834,392, granted to Lampman et al on Sept. 10, 1974, there is disclosed a laparoscope system for sterilization whereby a single unit contains the power source to provide illumination, oscillatory electrical power, and $CO_2$ gas for laparoscopy. The $CO_2$ gas under pressure is first passed into the body through a needle into the peritoneal cavity. A trocar and cannula are inserted into the gas-filled abdominal cavity. A telescope connected to a source of illumination is inserted into the body cavity through the cannula. The anatomical tubes are then identified through the laparoscope. Flexible forceps are thereafter inserted through the laparoscope into the body cavity. The forceps are manipulated to successively close the passage through each tube either by means of sending electrical oscillation through the forceps to simultaneously cut, seal, and cauterize each tube in turn, of by means of a specific clamp, which clamps the passage shut.

Also, a ring applicator device is disclosed in U.S. Pat. No. 3,989,049 to In Bae Yoon, granted on Nov. 2, 1976. The Yoon device is used for applying an elastic occluding ring to an anatomical tubular structure. The Yoon device comprises an inner cylinder slidably disposed within an outer cylinder, forceps means slidably disposed within said inner cylinder, means for moving said forceps means into and out of the inner cylinder and means for ejecting an elastic ring from the end of said inner cylinder by axially displacing said outer and inner cylinders relative to each other.

Heretofore, male sterilization by the use of clamps or elastic rings has been quite popular, however, there are certain inconveniences and dangers associated with elastic ring sterilization. This type of sterilization usually requires some cutting of the patient accompanied by a period of hospitalization. Furthermore, in any type of medical procedure requiring incision there is always the possibility and danger of infection.

Another technique used in the sterilization of the male is that of electro-surgery. Electro-surgery involves conducting a high frequency current, typically a radio-frequency current to the male vas in a manner to burn off certain portions of the tubes.

The method of electro-surgery heretofore used has involved an electrocautery apparatus operated with a monopolar current flow, in which the forceps conduct a radio frequency current (RF) from the source to the anatomical tube, after which the current flows from the anatomical tube through the patient's body to an electrode strapped on the patient's leg or elsewhere and thereafter to the ground.

Again, this procedure may also require some period of hospitalization. Furthermore, there have been other difficulties encountered in electro-surgery. For example, if the electrical path between the patient's body and ground should be poor or if it should be broken for any reason, the patient is frequently burned on whatever part of his body might be touching or close to the operating table, since the high frequency energy will seek the shortest path to the ground. Also, electro-surgery tends to dry out the effective tissue, thus cutting off the possible path of electrical current. With the current path cut off, current flow occurs in random directions away from the operation site, and thus causes burns of other tissue adjacent to the anatomical tube being treated.

In both of the above discussed sterilization techniques, parts of the body other than those which are to be treated may be burned, cut, or damaged.

It is accordingly an object of this invention to provide a means for accomplishing male sterilization and to avoid the problems of the techniques heretofore used.

It has surprisingly been discovered that male sterilization can be accomplished, without the need for incision or cauterization and their accompanying inconveniences and dangers, by the use of the method of the present invention. In utilizing the apparatus of the present invention, a surgeon exposes the anatomical element to be treated to electromagnetic radiation which is absorbed by the element causing the element to rise in temperature to a sufficient degree for coagulation thereof. In utilizing the present invention, for example in sterilizing the male vas, the surgeon would grasp that portion of skin to which the vas is closely adjacent and thereby manipulate the skin around the vas. The vas and the surrounding skin are disposed in the sterilization apparatus and exposed to electromagnetic radiation for coagulation of the vas. This procedure involves no incision or cauterization nor is there any damage to the grasped skin or any adjacent body elements. Since such a sterilization procedure requires no healing period, e.g. healing of an incision, and is itself relatively simple, no extended time in the hospital is needed. Thus, the method of the present invention does provide a very significant advancement in the field of sterilization.

Treatment with electromagnetic radiation has in recent years found applications in the treatment of cancerous organs. In such treatment, electromagnetic radiation impinges the body and is directed towards the cancerous tissue. Some of the electromagnetic radiation will be attenuated as it travels through the body to the cancerous tissue. Depth of radiation penetration into the body is a function of the radiation frequency as well as tissue absorption. The amount of radiation absorbed by tissue is dependent on the chemical composition of the tissue. Thus, the composition of both the cancerous tissue as well as the tissue through which the radiation passes in reaching the cancerous tissue must be known and understood.

With the proper frequency selected for the particular tissue to be treated, the electromagnetic radiation penetrates the body and is substantially absorbed by both normal and cancerous tissue. However the cancerous tissue reacts differently than the normal tissue and is more readily affected or destroyed. The tolerance of internal organs of mammals to temperature change is very limited. An elaborate biological mechanism exists to maintain the internal temperature of hot-blooded animals within well defined limits. In typical cancer treatment, to which we make reference, the tissue temperature is usually raised about 5 or 6 degrees. This rise in tissue temperature does not cause any permanent damage. Normally the body organs are at about 38° C., and in such treatment are typically raised to a temperature of about 44° C. It has been discovered that this small elevation in tissue temperature often results in either the retarding of the cancerous growth or its self-destruction.

To the present time, radiation exposure has primarily focused on cancer treatment. In such application the radiation must be of a frequency which can penetrate deep into the body. Furthermore, such treatment is directed to relatively large areas of tissue which are raised only a few degrees in temperature by radiation exposure.

The method of the present invention deviate from the major thrust of most radiation treatment. The present invention is concerned with changing or destroying the chemical and/or cell structure of relatively small areas of the body, and furthermore, utilizes electromagnetic radiation at a higher frequency than heretofore used, resulting in relatively shallow radiation penetration through the tissue with selective heating effect of fatty and muscular tissue. These and other objects are accomplished by the method of the present invention in selective applications for example, male sterilization by coagulation of the vas.

SUMMARY OF THE INVENTION

The apparatus used in the method of the present invention for treating or coagulating anatomical elements includes a body having two members which are constructed to hold an anatomical element therebetween. Mounted on at least one of the body members is a waveguide means constructed for the emission of electromagnetic radiation from a surface thereof. The emitted electromagnetic radiation is of a predetermined microwave frequency or range of frequencies suitable for treating or coagulating an anatomical element. Also, alignment means are provided on at least one of the body members. The alignment means is adapted for alignment of the waveguide emission surface with an anatomical element held between the body members so that the emitted electromagnetic radiation of the waveguide means will impinge on and penetrate the held anatomical element and thereby cause it to be treated.

In one method of the present invention using an instrument as described above, the anatomical element is first supported and held between the body members thereafter electromagnetic radiation is emitted from the waveguide means and falls upon the held anatomical element. The element is subjected to the emitted waveguide radiation for a period of time resulting in coagulation or treatment of the held portion. It is advantageous to maintain a predetermined pressure on the anatomical element to insure the desired result on a predictable and duplicable basis.

BRIEF DESCRIPTION OF THE DRAWINGS

FIG. 1 is a side elevational view of one embodiment of the apparatus used in the method of the present invention.

FIG. 2 is a cross-sectional view of the radiation detecting means carried on the apparatus used in the method of the present invention.

FIG. 3 is a cross-sectional view of the waveguide means carried on the present invention.

FIG. 4 is a view along the line 4—4.

FIG. 7 is an elevational drawing as viewed along the line 7—7.

DETAILED DESCRIPTION OF THE INVENTION

Figure 5:
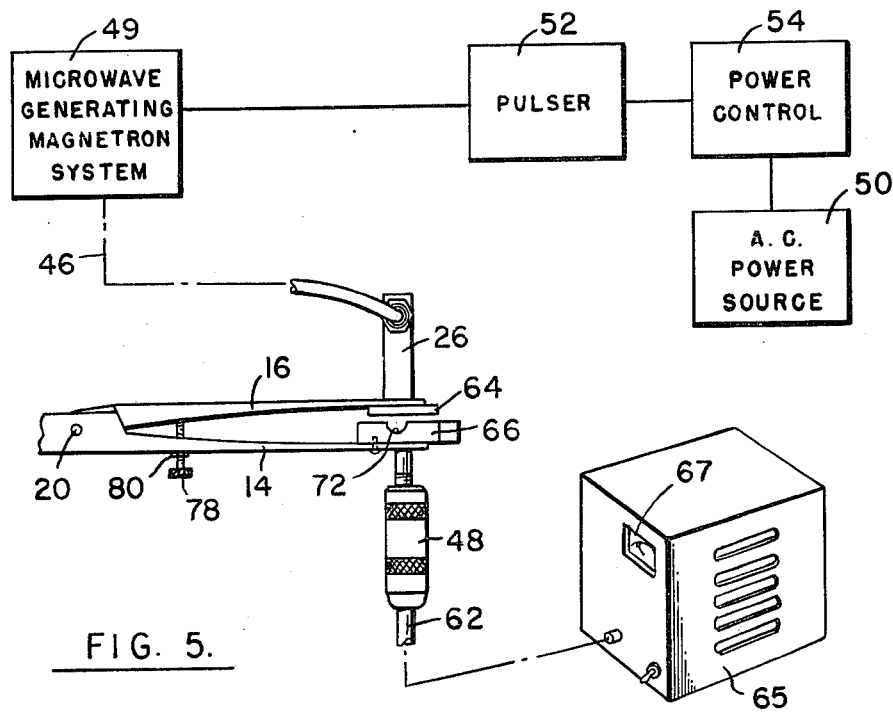
FIG. 5 is a schematic drawing including the apparatus used in the method of the present invention.

Referring to FIGS. 1 to 5, the sterilization apparatus used in the method of the present invention is generally designated as 10. Apparatus 10 includes a body 12 of a generally scissors-like structure having two elongated members 14 and 16 pivotable about an axis 20.

At one distal end of each of the body members 14 and 16 are gripping means 22 and 24 respectively. Gripping means 22 and 24 are shown as being in the form of loops to accommodate the operating surgeon's thumb and index finger, although other conventional shapes can be used for the operation of the present invention.

Carried on the distal end of body member 16 opposite gripping means 24 is a waveguide 26 disposed in an upright position thereon. Waveguide 26 contrains or guides the propagation of electromagnetic waves along a path defined by the physical construction of the waveguide.

Waveguide 26 includes four slanting sidewalls 28 and a back wall 30 of a metallic material reflective to electromagnetic radiation, such as copper or silver. The body 32 of waveguide 26 is filled with a material of high dielectric constant (K) such as magnesium calcium titanate. As subsequently described in detail, the electromagnetic radiation propagates along waveguide 26 in the direction of arrow 33. The surface of body 32 opposite back wall 30 is polished to a smooth finish and is the emission surface 34 of the waveguide 26. The waveguide 26 is typically impedance matched to human tissue.

A coaxial plug 36 (shown as a female plug) is mounted on one wall of the waveguide 26. Plug 36 is externally threaded. A wire 38 of high electrical conductivity extends through the body 32 and is in electrical contact with wall 28 while its opposite end extends into the passageway 40 of the coaxial plug 36.

A coaxial plug 42 (shown as a male plug) mates with and is fastened to female coaxial plug 36 by a nut 44. A coaxial cable 46 is seated in plug 42 and makes electrical contact with wire 38. Cable 46 extends to and electrically plugs into a magnetron microwave power generator 49 (plugs not shown), which is the source of microwave energy. Also, other sources of microwave energy can be used, e.g. solid state generators. The magnetron 49 is of a conventional construction such as model 10MBL built by Mictron, Inc. of Sarasota, Fla. Magnetrons in general are built to deliver microwave power at a predetermined frequency and at a predetermined voltage. Magnetron 49 is operated from an AC power source designated as 50. In order to have the capability of varying the power level of magnetron 49, its power output is controlled by a pulser unit 52 which is in turn controlled by a power control means 54. Pulser unit 52 is of conventional circuitry design and make possible the pulsing of the magnetron, i.e. by varying its pulse duration or duty cycle, so that the power of the magnetron can be lowered from or raised to the power output for which it was designed.

In the operation of the waveguide 26, after the magnetron 49 and its associated apparatus have been activated, a microwave current flows through the wire 38 and electromagnetic energy generated from wire 38 will flow towards the emission surface 34, while some of the emitted microwave energy will flow in the opposite direction and strike the back wall 30. However, the waveguide 26 has been designed so that the distance between the wire 38 and the back wall 30 is equal to one quarter the wavelength of the emitted radiation. According to well known laws of wave propagation and reflection, the electromagnetic radiation striking back wall 30 will be substantially reflected and guided towards the emission surface 34. Thus, substantially all of the generated electromagnetic radiation is emitted from surface 34.

The dimensions of waveguide 28, and in particular those of emission surface 34, are determined according to the frequency at which the electromagnetic radiation is emitted. However, the dimensions of waveguide 28 and in particular the emission surface 34 are reduced by making dielectric body 32 of a material with a high dielectric constant as noted above. This is advantageous in that it reduces the size of the apparatus 10 in general, thereby making the instruments operation practical for treatment of small areas of body tissue.

Mounted on an end of body member 14 opposite the gripping means 22 is a microwave energy detector 48. Detector 48 includes a cylindrical housing 50 comprising an elongated member 52 screwed onto a base member 54. Extending from base member 54 is tubular member 56 which is mounted directly to the distal end of body member 14. A probe 58 (a highly conductive wire) extends from body 50 through tubular member 56. Probe 58 is bent at a 90° angle at its distal end, and it is this end of probe 58 which is in contact with or adjacent to the anatomical element being treated.

Probe 58 functions somewhat like an antenna during the operation of the present invention and senses any microwave electromagnetic radiation which completely penetrates the treated anatomical element.

Figure 6:
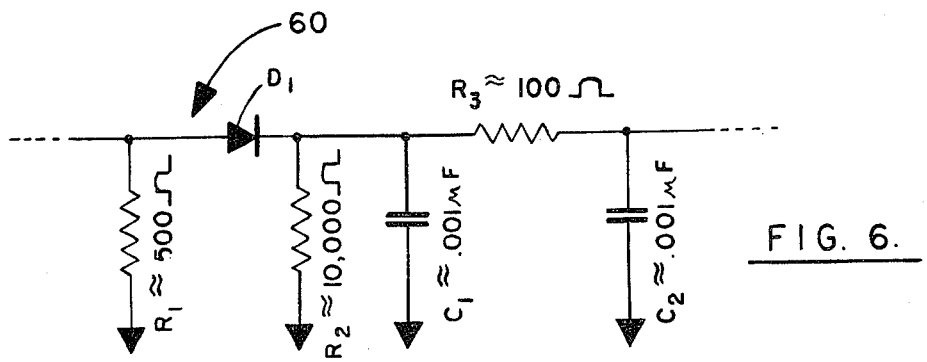
FIG. 6 is an electrical schematic, showing the circuitry of the filter carried in the detecting means shown in FIG. 2.

The electromagnetic radiation sensed by probe 58 is rectified by a diode $D_1$, then through a filtering circuit designated as 60. The diode $D_1$ may be for example an HP3082-2810. As is well understood by those in the field of electronics, coaxial cable 62 may be of a substantial length and therefore act somewhat like a capacitor. Thus, the filtering circuit 60 has been provided to filter out any of the electromagnetic radiation of the frequency of emitted waveguide 26 radiation. Filter circuit 60 is of a conventional design as shown in FIG. 6 which describes the various components and their respective values.

Thereafter, the filtered signal is sent by a coaxial cable 62 to an amplifier 65 having a meter 67. Thus, the operating surgeon can view the meter 67 and determine therefrom if emitted waveguide 26 radiation has penetrated the grasped anatomical element. Furthermore, a correlation can be found between the meter 67 reading and the instant at which coagulation of the held anatomical element has been completed. Such correlation is a function of frequency of the electromagnetic radiation emitted from waveguide 26 and the thickness and the nature of the tissue through which it must penetrate before being detected by sensing means 48.

Mounted inwardly on the distal end of body member 16 is a waveguide plate 64. Likewise, a sensing detector plate 66 is mounted on the distal end of body member 14. Waveguide plate 64 includes an opening 68 (as shown in FIG. 4) in alignment with and of dimensions at least as large as the dimensions of the emission surface 34. The sensing means plate 66 includes an opening designated as 70, which mates with tubular member 56 of detector 48. One or more grooves 72 are formed on the inward surface of plate 66 to support, accommodate and prevent slippage of the anatomical element held between the closed body members 14 and 16. If, for example, two grooves 72 are used, they may be perpendicular to each other as shown in FIG. 7, to accomodate the anatomical element in a position most convenient to the operating surgeon; although it is anticipated that the grooves 72 may be at any angular relationship to each other. Upon closing of the body body members 14 and 16 about an anatomical element diposed in groove 72, the grasped anatomical element is aligned with the emission surface 34 of waveguide 26 and probe 58 of detector 48. Thus, plate 66 also acts as an alignment means. However it is further anticipated that both plates 64 and 66 may have complementary grooves 72 therein to accomodate a grasped anatomical element, and therefore both plates 64 and 66 function as alignment means.

To control the extent upon which the body members 14 and 16 close upon each other, a screw member 78 is screwably mounted to body member 14 in the vicinity of axis 20 and is adjustable in its movements towards body member 16. Thus, as body members 14 and 16 close upon each other, body member 16 will encounter the end of screw 78 thereby preventing any further closure. Screw member 78 thereby prevents unnecessary pressure being applied to the grasped anatomical element. Once the surgeon has completed adjustment of screw member 78, it is locked into position by locking nut 80. Furthermore, once the body members 14 and 16 have been closed towards each other, to securely hold the anatomical element therein, a locking means 82 is engaged. Locking means 82 may be of any conventional type, such as the ratchet shown in FIG. 1.

The application of the present invention is ideally suited for those situations where it is desirable to coagulate, i.e. chemically alter and thereby destroy, an anatomical element and wherein the electromagnetic radiation used for such purpose is only required to penetrate a short distance through body tissue, i.e. 5 to about 20 millimeters.

For the purpose of describing the operation of microwave sterilization apparatus 10, it is subsequently explained with reference to coagulation of the male vas, thereby rendering the individual sterile.

In using the apparatus 10 for coagulation of the male vas, the vas is exposed to and absorbs electromagnetic radiation at such power level and for a period of time that its temperature is raised in the range of 55° to 80° C.

Electromagnetic radiation at a frequency of about 6 GHz is highly suited for coagulating a vas using the sterilization apparatus 10 for reasons subsequently discussed. As has been well documented by those researching electromagnetic radiation therapy, the ratio of absorption of microwave energy in fat tissue compared to muscle tissue is dependent on frequency and is much lower at a frequency of 6 GHz then at lower microwave frequencies. The composition of human skin varies over different parts of the body. However, in the area of the vas and in other selective areas, the skin is approximate in composition to that of fatty tissue, i.e. lower in its content of water and salts, whereas the vas more closely resembles muscle tissue in its composition, i.e. high in water and salt content. Six gigahertz is a good compromise between selective absorption and the cost of presently available microwave generating equipment.

Figure 8:
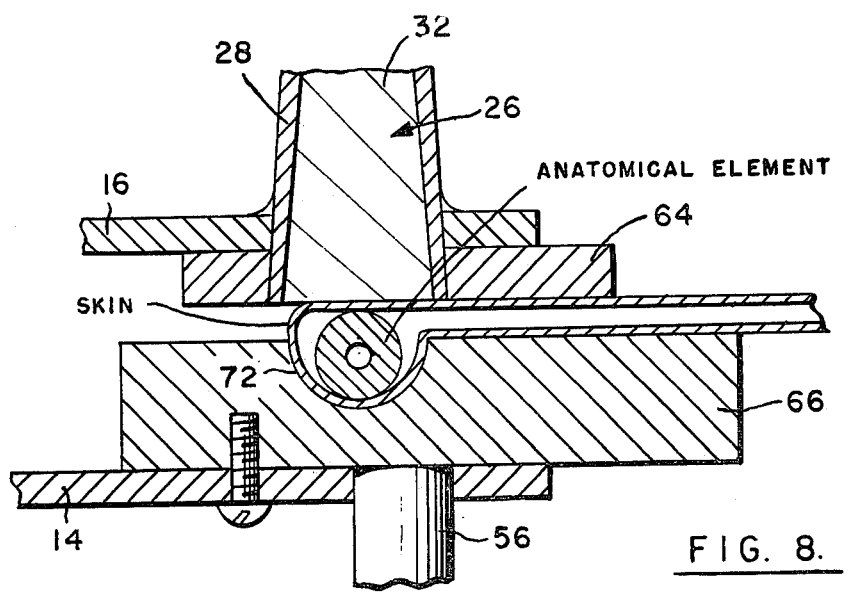
FIG. 8 is a cross-sectional view showing an anatomical element held in the present invention.

Since the male vas is close to the skin's surface, in the operation of the present invention, the surgeon grasps this area of skin thereby surrounding the vas with the skin, i.e. scrotum, referring to FIG. 8. The vas and its accompanying layer of skin are thereafter disposed in groove 72 of alignment plate 66. Body members 14 and 16 are closed towards each other to hold therebetween the vas and its accompanying layer of skin. Apparatus 10 is locked into its holding position by ratchet 82 so as to maintain a given pressure on the vas. Magnetron 49 with power supply 50, pulser unit 52 and power control means 54 are then activated for generation and emission of electromagnetic radiation from emission surface 34. The emitted radiation impinges on the vas and the surrounding skin. As described above, the skin being more like fatty tissue absorbs a little of the emitted electromagnetic radiation while most of the radiation is absorbed by the vas. Since the vas is absorbing most of the emitted radiation, it is heated to a higher temperature than the skin which absorbs less of the radiation. The vas is allowed to heat to a temperature of about 55° to 80° C. thereby causing its coagulation. The skin may feel hot to the touch, but this is primarily from heat being conducted to the skin from the vas and will not reach coagulation temperature if the power level and the duration of the power application has been properly adjusted.

Typically, the vas is coagulated by heating it with the electromagnetic radiation for a minute or less, however the length of time required to cause vas coagulation is a function of the electromagnetic radiation power. The greater this power the more rapidly coagulation will occur. Conversely, the lower the power the longer the period of time needed for the vas to reach coagulation temperature. It has been further discovered that there is a threshold of electromagnetic radiation which must be exceeded in order to reach coagulation temperature. This threshold of power is usually a function of the field configuration in the waveguide, the frequency of the waveguide radiation emission, the tissue which is being treated and its thickness.

Most of the waveguide emitted radiation will of course be attenuated as it travels through the vas, however at least some of the radiation will penetrate the vas and is sensed by probe 58 of the detecting means 48. A reading on meter 67 of amplifier 65 will indicate that electromagnetic radiation has impinged and penetrated the vas. However, it has been further discovered that the meter reading will steadily increase with a constant power input, but once the vas has coagulated, there is a sudden dip in the meter reading. Thus, an operating physician viewing meter 67 can determine vas coagulation upon sensing a decrease in the meter reading.

Figure 9:
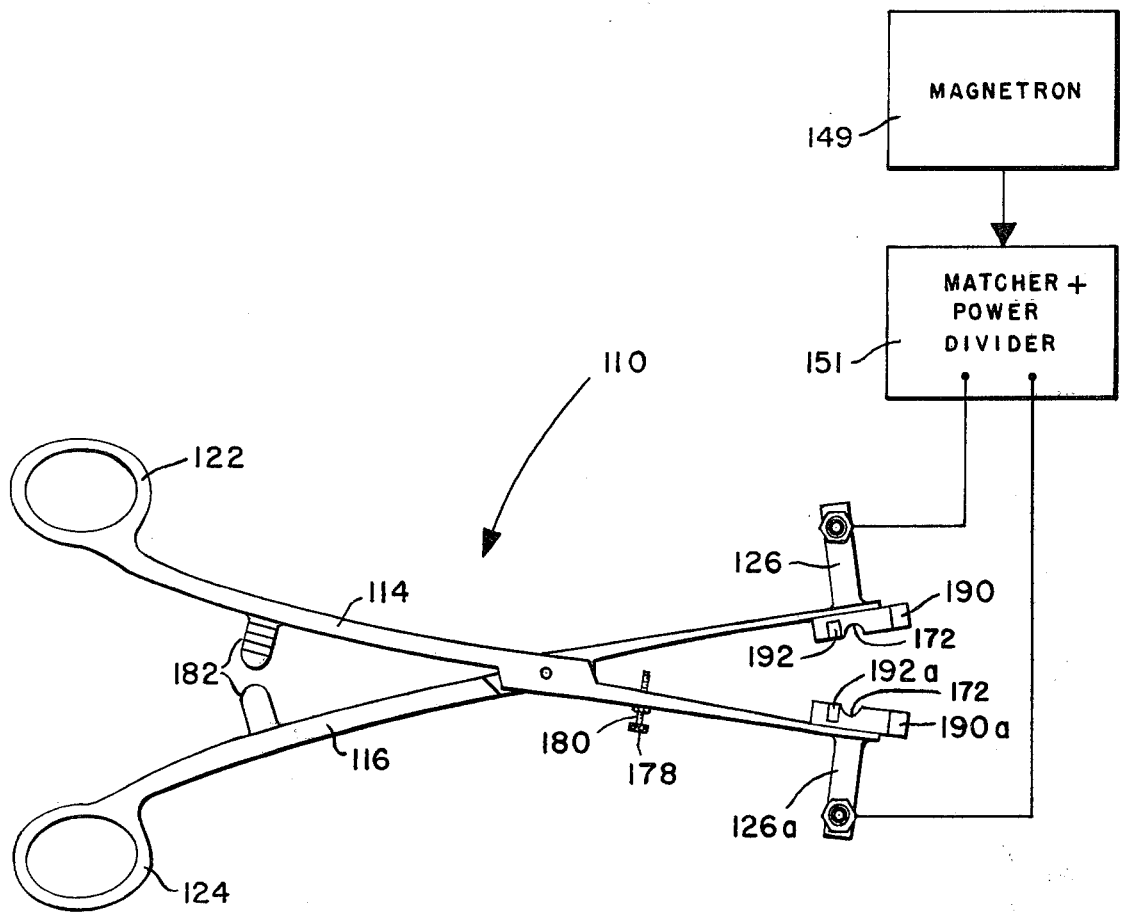
FIG. 9 is a second embodiment of the sterilization apparatus used in the method of the present invention.

Referring to FIG. 9, a second embodiment of the present invention designated 110 is shown therein. Apparatus 110 is very similar to apparatus 10 of the first embodiment and elements 114, 116, 122, 124, 126, 178, 180, 182, are the same as elements 14, 16, 22, 24, 26, 78, 80, and 82 of the first embodiment 10.

The second embodiment differs from the first embodiment in that it includes waveguides 126 and 126a on both of the distal ends of body members 114 and 116 respectively. Each waveguide is powered by a microwave power source such as magnetron 149 through a power-matcher-directional-coupler-divider 151. Thus, each of the waveguides 126 and 126a only receives half of the power output of the magnetron 149. The advantage of this embodiment is that since each of the waveguides is emitting electromagnetic radiation of only one-half power, the skin on either side of the held vas is exposed to radiation at one-half the power. Thus, the skin will be heated with this embodiment to a lesser degree than if one used the first embodiment. Also, the radiation absorbed by the vas from both waveguides is cumulative, thus the vas will absorb as much radiation as it did with the first embodiment.

The waveguide alignment plates 190 and 190a are similar to the alignment plates in the first embodiment and further include complementary grooves 172 for proper alignment. In addition, thermistors are recessed in each of the alignment plates 190 and 190a so that they come in contact with the skin surrounding the vas and thereby sense the skin temperature. A correlation can be found between an increase in skin temperature largely through thermal conduction from the vas (even though it may only be a few degrees) corresponding to the temperature at which the vas coagulates. Furthermore, an alternative procedure is to provide small piercing probes attached to the thermistors 192 and 192a, for piercing through the skin and sensing the vas temperature directly.

Figure 10:
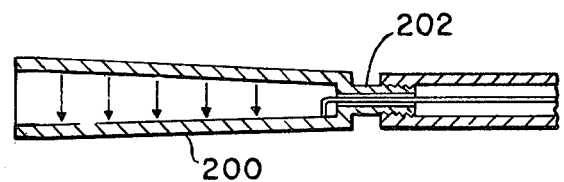
FIG. 10 is a cross-sectional view of a circular or elliptical waveguide which can be used in the operation of the present invention.

While the waveguides in both of the embodiments have been described as being rectangular in shape, it is also anticipated by the present invention that the waveguides may be circular or elliptical in form as shown in FIG. 10, using high dielectric material to reduce the physical size as in the above description.

As to the circular or elliptical waveguide 200, a coaxial plug 202 is mounted thereon and is coaxial therewith using one mode of coupling (TE) as shown. Other modes of coupling may be used to provide TE and TM waves of higher order. This allows the use of various sizes of electrodes and various patterns of coagulation.

While an advantage of the present invention is that it can be used to sterilize the male without the need of an incision, nevertheless it is further anticipated that the present invention can be utilized where an incision has been made in the scrotum exposing the vas. Thereafter, the vas is held by the instrument of the present invention and subjected to microwave radiation for coagulation thereof.

Although this invention has been described with reference to specific embodiments thereof, it will be appreciated that various other modifications may be made, including a substitution for those shown and described. Further, the invention comprehends the use of certain features independently of other features, reversals of parts and the substitution of equivalent elements, all of which modifications may be made without departing from the spirit and scope of the invention as defined in the appended claims.

I claim:

1. In a method for sterilizing a male by coagulation of the vas without incision, cauterization or harm to the scrotum adjacent to the vas and further without subjecting the male to the dangers and inconveniences accompanying incision or cauterization, including the use of an instrument having a body with spaced-apart members adapted for closing towards each other and holding a vas and surrounding scrotum skin therebetween, and a waveguide means impedance matched to human tissue constructed to emit radiation at a predetermined microwave frequency suitable for coagulation of the vas, said waveguide means disposed in at least one of said body members and having a radiation emission surface disposed in a face of said body member including said waveguide means, comprising the steps of:

(a) manipulating the scrotum around the vas to substantially closely surround said vas with said scrotum skin;

(b) placing only said vas and said surrounding scrotum skin between said body members;

(c) closing said members towards each other until said members including said waveguide means gently contact respective outer surface portions of said scrotum skin surrounding said vas, said emission surface contacting said surrounding skin;

(d) emitting electromagnetic radiation from said waveguide means radiation emission surface locally towards and through said scrotum skin and the vas surrounded thereby in a direction towards said remaining body member;

(e) subjecting only the contacted scrotum skin and the vas surrounded thereby to said locally emitted radiation for a period of time to substantially increase the temperature of said vas and thereby coagulate the vas, said surrounding scrotum skin temperature being increased to a lesser degree than said vas so that said surrounding scrotum skin is essentially unharmed.

2. In a method for sterilizing a male by coagulating an anatomical element using an instrument having a body with two members adapted for closing towards each other and holding therebetween an anatomical element, and a waveguide means constructed to emit electromagnetic radiation at a predetermined microwave frequency suitable for coagulation of an anatomical element, said waveguide means disposed on at least one of said body members, comprising the steps of:

holding an anatomical element between said body members closed towards each other at a predetermined pressure;

causing emission of electromagnetic radiation from said waveguide means in one of said body members towards the remaining body member, said radiation being emitted at a frequency to selectively permanently cauterize only muscle tissue portions of said anatomical element held between said body members without significant damage to fatty tissue portions of said anatomical element held between said body members; and subjecting the held anatomical element to said emitted waveguide radiation for only a period of time sufficient to coagulate said muscle tissue portions of the anatomical element.

3. In a method for sterilizing a male by coagulating an anatomical element using an instrument having two body members adapted for holding an anatomical element therebetween, waveguide means carried on at least one of said body members so that electromagnetic radiation emitted therefrom impinges on an anatomical element held between said body members, said emitted electromagnetic radiation being of a predetermined frequency for coagulation of a held anatomical element, and electromagnetic radiation sensing means on the other of said body members, the steps comprising:

temporarily retaining an anatomical element between said body members;

activating electromagnetic radiation emission from said waveguide means, said radiation being emitted at a frequency to selectively cauterize only muscle tissue portions of said anatomical element without significant damage to fatty tissue portions of said anatomical element when said radiation is applied to said anatomical element for a period sufficient to cauterize muscle tissue portions of said anatomical element but only to heat skin tissue portions of said anatomical element without significant damage thereto;

causing said emitted electromagnetic radiation to impinge and penetrate the held anatomical element but only for said period of time sufficient to coagulate said muscle tissue portions of the anatomical element; and directly detecting the electromagnetic radiation which penetrates through the anatomical element, thereby sensing that the emitted radiation is impinging on the anatomical element; and halting the application of radiation when the detected level of radiation drops substantially thereby indicating that cauterization of said muscle tissue portions of said anatomical element has occurred.

4. In a method for sterilizing a male by coagulation of the vas using an instrument having a body with two members adapted for closing towards each other and holding therebetween said vas and adjacent skin, and waveguide means constructed to emit radiation at a predetermined microwave frequency suitable for selective coagulation of a vas but not the skin theresurrounding, said waveguide means disposed on at least one of said members, comprising the steps of:

manipulating skin adjacent said vas to substantially surround said vas;

placing said vas and surrounding skin between said body members and closing said members towards each other to position said vas and skin to receive radiation directly from said waveguide means;

causing emission of electromagnetic radiation from said waveguide means; and subjecting the held skin and the vas theresurrounded to said emitted radiation for a period of time to substantially raise the temperature of said vas and thereby coagulate said vas without corresponding substantial temperature increase of said surrounding skin.

5. The method in accordance with claim 4, wherein said vas temperature being raised to the range of 55° to 80° C.

6. The method of claim 2 or 3 or 4, wherein said radiation has frequency of from about 4 to about 7 gigahertz.

7. The method of claim 6 wherein said radiation has frequency of about 6 gigahertz.

8. In a method for sterilizing a male by coagulating the vas using an instrument having a body with two members adapted for closing towards each other and holding therebetween a vas, and a waveguide means constructed to emit electromagnetic radiation at a predetermined microwave frequency suitable for coagulation of the vas, said waveguide means disposed on at least one of said body members, comprising the steps of:

performing an incision in the scrotum adjacent the vas and exposing said vas;

holding said vas between said body members closed towards each other;

causing emission of electromagnetic radiation from said waveguide means;

subjecting said held vas to said emitted waveguide radiation for a period of time to coagulate said vas; and suturing said incision.

9. A method for sterilizing a male by selective coagulation of only the vas without scrotum skin incision, comprising the steps of:

(a) manipulating the scrotum skin around said vas;

(b) placing said vas and said skin adjacent to a first positioning member;

(c) urging a second positioning member against said skin and towards said first positioning member thereby entrapping said vas between portions of said skin and entrapping said skin and vas between said two positioning members;

wherein at least one of said positioning members includes a microwave radiation emission surface and said positioning means are configured to place said entrapped vas proximate said emission surface;

(d) emitting microwave radiation from said emission surface through said skin proximate said emission surface and into said vas;

(e) sensing residual radiation passing through said vas and emanating from said skin at a position remote said emission surface;

(f) halting emission of radiation when the time rate of change of sensed residual radiation changes.

10. The method of claim 9 wherein step (f) comprises halting emission of radiation when the level of sensed resident radiation drops thereby indicating substantial coagulation of said vas has occurred.

11. The method of claim 9 wherein said radiation is emitted at a frequency of from about 4 to 7 gigahertz.

12. The method of claim 11 wherein said radiation is emitted at a frequency of about 6 gigahertz.

13. In a method of sterilizing a male by coagulating the vas attached to the testes without substantially harming the scrotum skin adjacent said vas and without incision of said skin, the step which comprises directing microwave radiation at said vas through said skin along a path remote from said testes from outside said skin at a frequency effective to cause permanent coagulation of said vas substantially exclusively of said skin for sufficient time to heat said vas to a temperature at which said vas coagulates.

* * * * *